United States Patent [19]
Maloney et al.

[11] Patent Number: 5,188,606
[45] Date of Patent: Feb. 23, 1993

[54] MULTIPLE SIZE INTRODUCER SLITTER

[75] Inventors: Thomas J. Maloney; Eugene J. Champeau, both of Plymouth, Minn.

[73] Assignee: Medamicus, Inc., Minneapolis, Minn.

[21] Appl. No.: 757,715

[22] Filed: Sep. 11, 1991

[51] Int. Cl.$^5$ ............................................. A61M 5/00
[52] U.S. Cl. ..................................... 604/161; 604/177
[58] Field of Search ............... 604/158, 154, 160, 161, 604/164, 177, 280, 166; 30/90.1, 90.4, 90.8

[56] References Cited

U.S. PATENT DOCUMENTS

| | | | |
|---|---|---|---|
| 3,359,978 | 12/1967 | Smith, Jr. | 604/161 |
| 3,910,272 | 10/1975 | Forberg | 604/161 |
| 4,631,059 | 12/1986 | Wolvek et al. | 604/161 |
| 4,985,018 | 1/1991 | Smith | 604/161 |
| 4,997,424 | 3/1991 | Little | 604/280 |

FOREIGN PATENT DOCUMENTS 2260061 7/1973 Fed. Rep. of Germany ...... 604/161

Primary Examiner—John J. Wilson
Attorney, Agent, or Firm—Clayton R. Johnson

[57] ABSTRACT

Each embodiment of the slitter includes a handle member having an arcuate section joined thereto, a knife blade, a clamp member having a lower arcuate portion, and a hinge for joining the clamp and handle members for hinged movement between catheter clamping and release positions, each of the arcuate section and arcuate portion having transversely opposite facing surface portions for clampingly engaging diametrically opposite surface portions of any one of the number of different outer diameter catheters, and at least one of the arcuate section and arcuate portion having a nose portion for entering between the clamped catheter and the introducer when the introducer is to be removed from the catheter without being moved over the proximal terminal end of the catheter. The knife blade is located radially outwardly of the surfaces that abut against the clamped cather and extends radially outwardly of the nose and is located rearward of the forwardmost part of the nose.

18 Claims, 6 Drawing Sheets

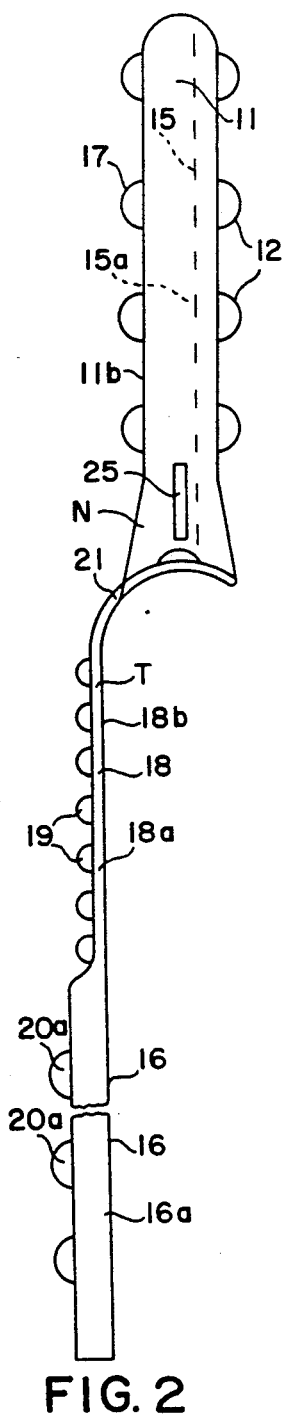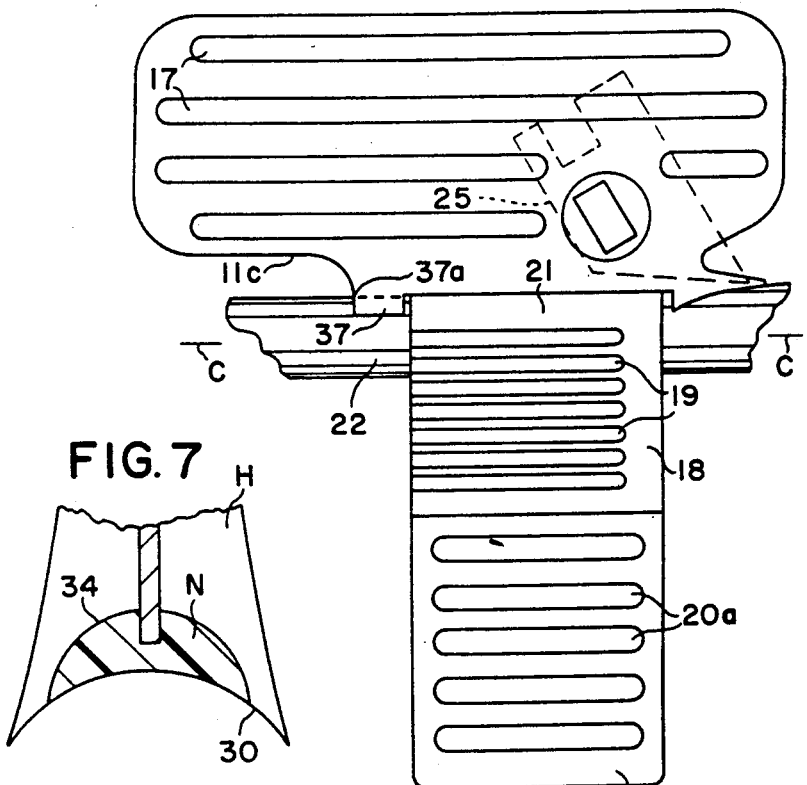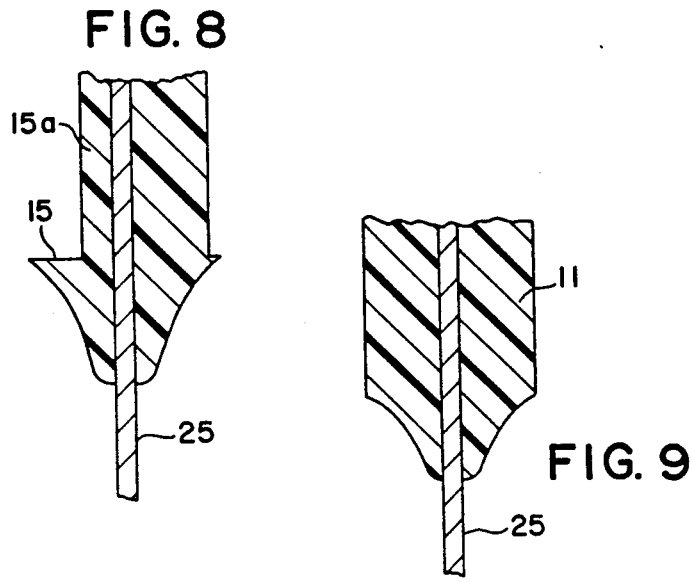

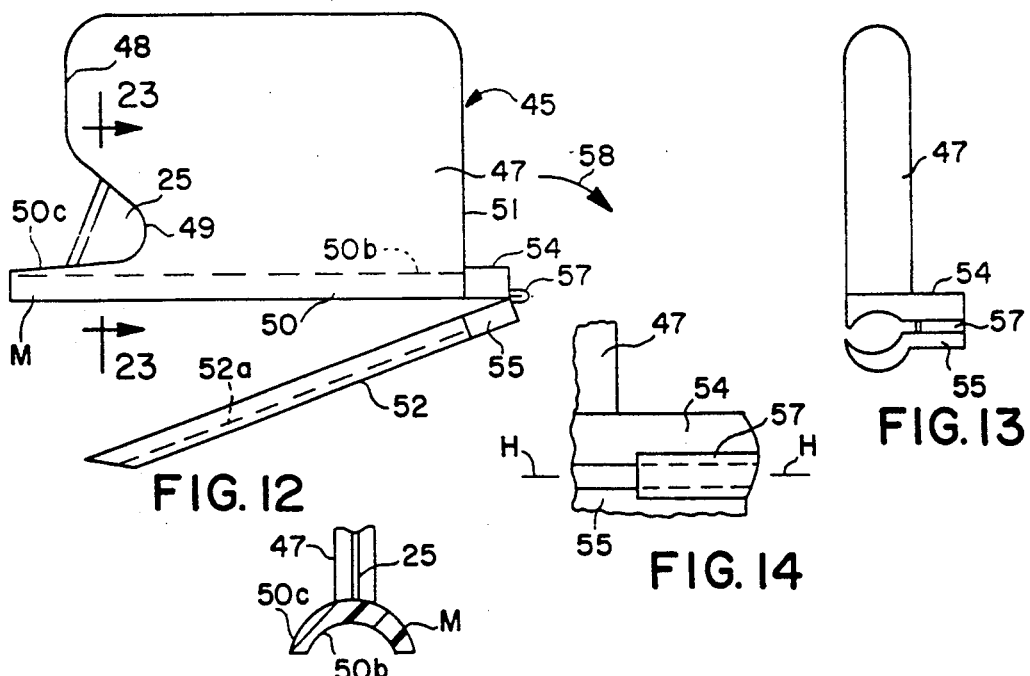
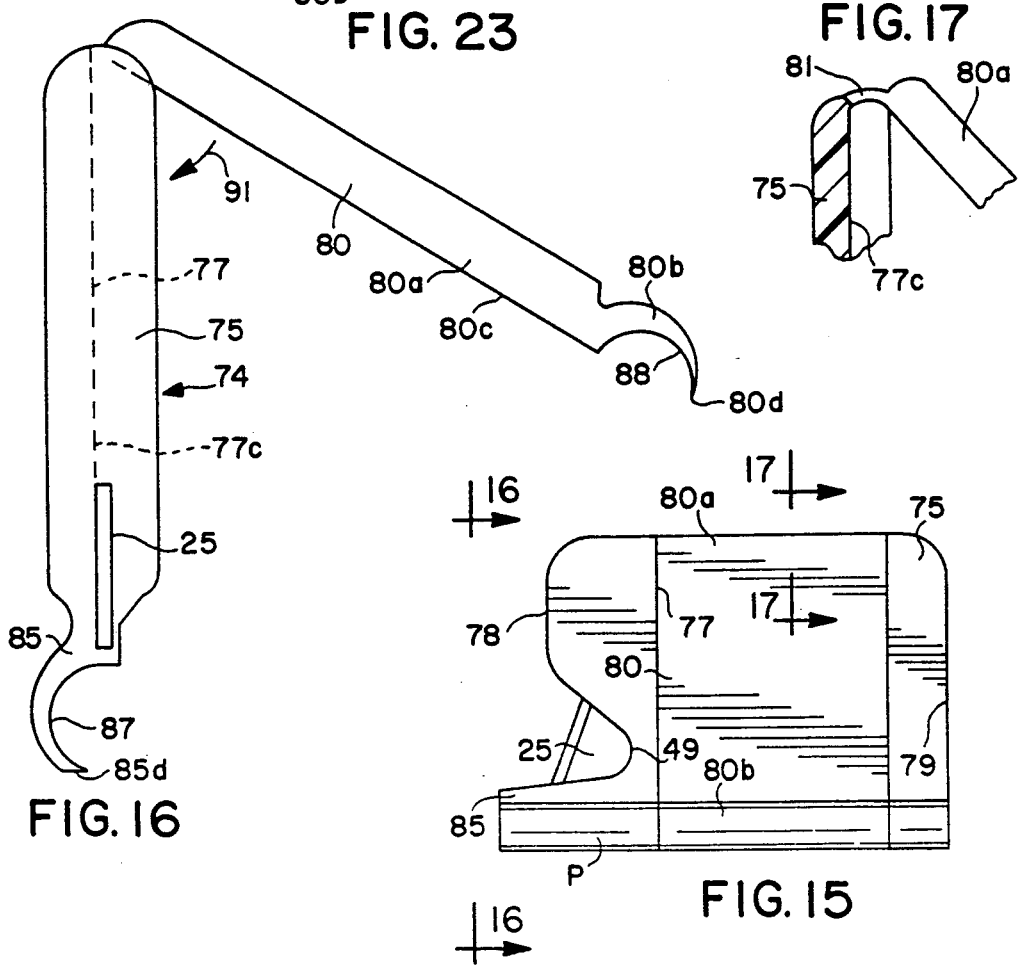

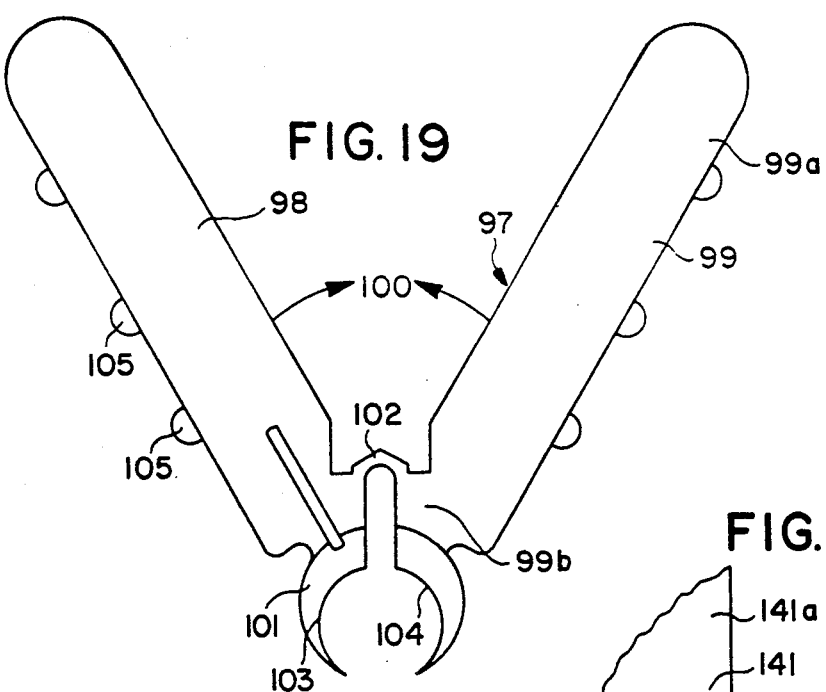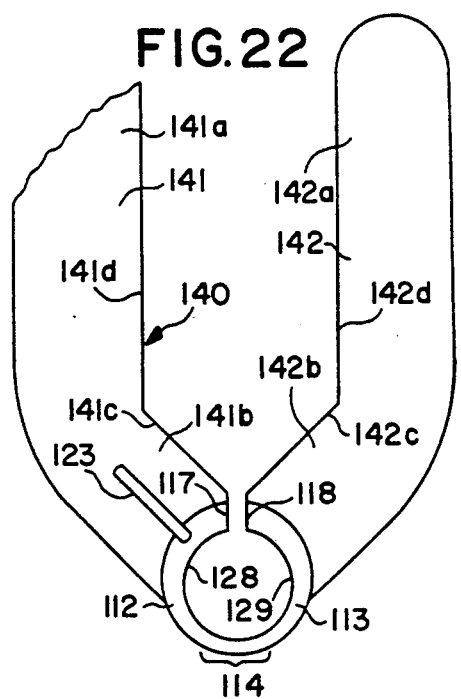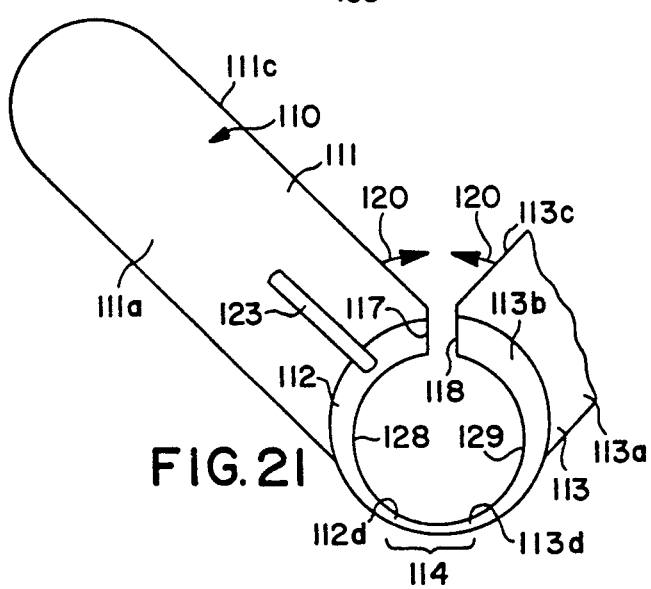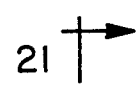

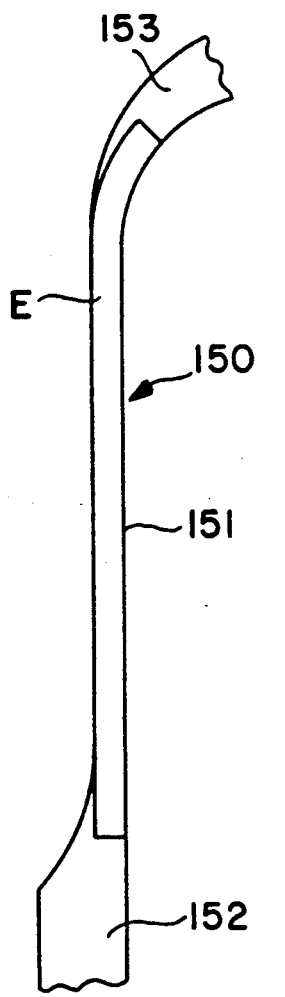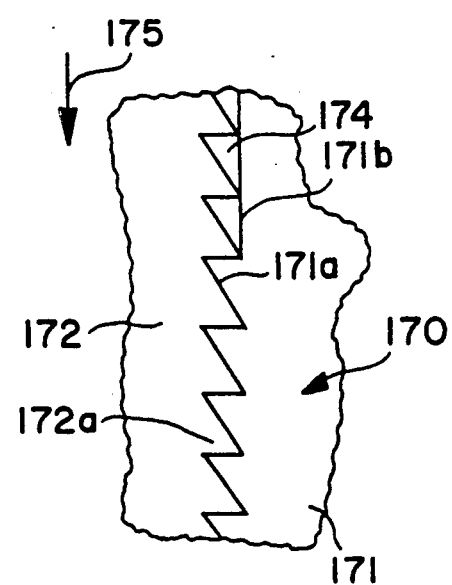
FIG. 24
FIG. 25

5,188,606

MULTIPLE SIZE INTRODUCER SLITTER

BACKGROUND OF THE INVENTION

This invention relates to the removal of an introducer or cannula from a catheter, pacing lead, or similar item without having to pull the introducer over the proximal end of the catheter, and more particularly to a slitter device that may be used for gripping any one of multiple number of different diameter catheters while the introducer is used for slitting an introducer.

In U.S. Pat. No. 4,997,424 to Little there is disclosed an introducer slitter having an arcuate section extending arcuately through at least 180° to extend partially around a catheter, a handle section joined to the arcuate section to extend away therefrom and a radially extending cutting edge for engaging the introducer tube portion as the introducer is pulled rearwardly relative to the slitter.

In U.S. Pat. No. 3,624,901 to Pettit there is disclosed a wire stripper and cutter that includes a handle that at one end has a cutting edge and a hooked shaped work support member that is pivoted to the handle adjacent to the cutting edge for supporting a cable as the insulation thereon is slit. One embodiment is adjustable to avoid having to provide hooks of different sizes for different diameters cables.

Huff, U.S. Pat. No. 2,141,002, discloses a cable stripper having a substantially semi-cylindrical body section that mounts a knife blade and hinge pins pivotally mounting gates to the body section. The finger and thumb pressure on the gates press them to a closed overlapping position while the palm of the same hand abuts against the body portion A knife blade extends radially inwardly of an angular surface that is abuttable against the cable radial outer surface.

In U.S. Pat. No. 4,631,059 to Wovek et al. there is disclosed a sheath remover having first and second separable body portions to form a bore to have the catheter extend therethrough and squeeze the sheath so that it extends into the path of movement of the cutting edge of the transversely extending knife blade. The two body portions are held together by a plastic hinge.

In order to provide an improved introducer slitter that may be used for slitting introducers for removing the introducers of any one of many different outer diameters catheters without initially having to be slid over the proximal end of the catheter and that is easily held while the slitter is being used, this invention has been made.

SUMMARY OF THE INVENTION

The introducer slitter is provided for longitudinally slitting a cannula or introducer to facilitate the removal of an introducer from a catheter extended therethrough wherein the catheter may be any one of many different outer diameter catheters. The slitter includes a handle section or main body having an arcuate section joined thereto, the arcuate section including a nose for extending between the introducer and catheter. The slitter also has a clamp portion and a hinge or strap section for joining the clamp portion to the handle section. The strap section of one embodiment provides a combined hinge and an arcuately curved clamp portion for extending partially around the catheter and clamping the catheter against the arcuate section to clampingly hold the catheter while the tubular portion of the introducer is being slit. The resilient hinge and arcuately curved clamp portion of other embodiments perform the same function as the strap section and handle section when firmly held between the user's forefinger and thumb to maintain the slitter in a fixed position relative to catheter. As a result of the length of the strap section the slitter may be used with catheters of many different outer diameters. A cutting edge is at least in part mounted by the main body for slitting the introducer as it is pulled along the catheter toward the slitter.

One of the objects of this invention is to provide new and novel means for clampingly holding a catheter while an introducer is being slit to separate the introducer from the catheter. In furtherance of the above object, it is a further object of this invention to provide an introducer slitter having new and novel means for connecting and moving the catheter clamping elements between a catheter clamping position and a catheter release position.

BRIEF DESCRIPTION OF THE DRAWINGS

FIG. 1 is a side view of the first embodiment of the slitter of the invention with its lower edge abutting against the top of the fragmentary portion of the catheter shown prior to the strap section being wrapped around the catheter;

FIG. 2 is an enlarged front view of the first embodiment of the slitter, an intermediate portion of the strap section along its length not being shown;

FIG. 7 is a fragmentary cross sectional view that is generally taken along the line and in the direction of the arrows 7—7 of FIG. 5;

FIG. 8 is a fragmentary cross sectional view that is generally taken along the line and in the direction of the arrows 8—8 of FIG. 6;

FIG. 9 is a fragmentary cross sectional view that is generally taken along the line and in the direction of the arrows 9—9 of FIG. 6;

FIG. 12 is a side view of the second embodiment of the slitter of this invention in a non-clamping position;

FIG. 13 is a rear end view of the structure of FIG. 12 other than the slitter is in a catheter clamping position;

FIG. 14 is an enlarged fragmentary portion of FIG. 13;

FIG. 15 is a side view of the third embodiment of the slitter of this invention;

FIG. 16 is a front end view of the slitter in a non-clamping position that is generally taken along the line and in the direction of the arrows 16—16 of FIG. 15;

FIG. 17 is a fragmentary cross sectional view of the slitter in a non-clamping position that is generally taken along the line and in the direction of the arrows 17—17 of FIG. 15 to more clearly shows the hinge;

FIG. 19 is a front end view that is generally taken along line and in the direction of the arrows 19—19 of FIG. 18;

FIG. 20 is a side view of the fifth embodiment of the slitter of this invention;

FIG. 21 is a fragmentary front end view generally taken along the line and in the direction of the arrows 21—21 of FIG. 20;

FIG. 22 is fragmentary front end view of the sixth embodiment;

FIG. 23 is a fragmentary cross section view that is generally taken along the line and in the direction of the arrows 23—23 FIG. 12.

FIG. 24 is a fragmentary cross sectional view of the strap portion seventh embodiment of the invention, and FIG. 25 is a fragmentary vertical cross sectional view of the strap and the strap recess of the main body of the eighth embodiment in a clamping position.

Figure 3:
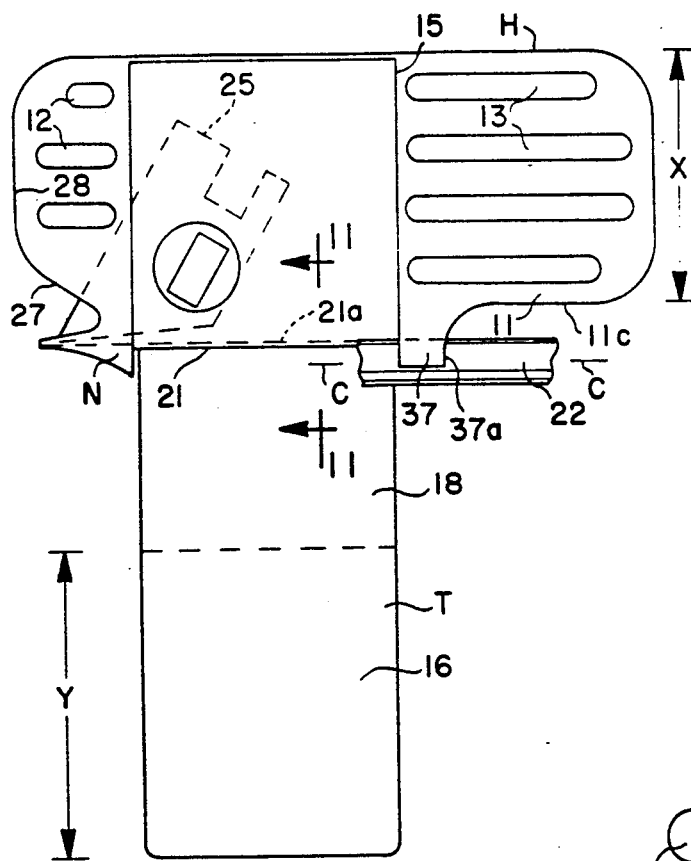
FIG. 3 is a side view of the first embodiment that is opposite the side shown in FIG. 1.
Figure 4:
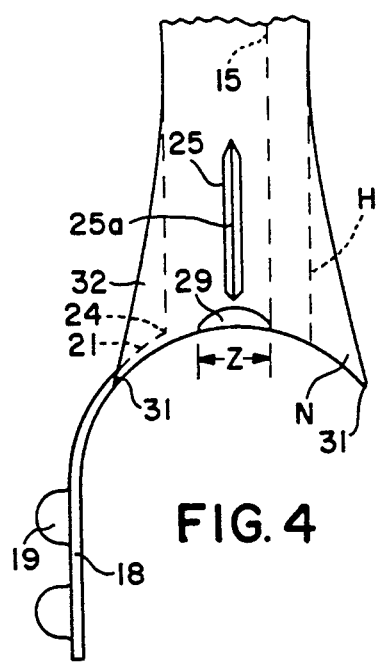
FIG. 4 is a further enlarged portion of part of the structure shown is FIG. 2.

Referring in particular to FIGS. 1–3, the first embodiment of the introducer slitter, generally designated 10, includes an axially elongated handle section H The handle section includes a main body (handle member) 11 that has a lower front edge portion integrally joined to the upper rear portion of the nose portion N of the arcuate section N, 21, 37 with the main body and is transversely centered relative to the nose portion. The main body 11 on one side has a plurality of axially elongated ribs 17 joined thereto while the opposite side has a plurality of front ribs 12 and rear ribs 13 axially spaced from the front ribs. A generally rectangular cut out (strap recess) 15 is provided in the main body axially intermediate the ribs 12, 13, is of an axial dimension slightly greater than the corresponding dimension of each of the handle element 16 and the strap section 18 (clamp portion) of the clamp member (strap) T, and advantageously of a depth about half to about the same as the thickness of the handle element 16. Further the cut out extends to open through each of the top and bottom edges of the main body. One axial end of the strap section is integrally joined to one edge of the handle element while the opposite axially extending end of the strap is integrally joined to portion 21 of the arcuate section that is axially aligned with the cut out. Portion 21 is located axially intermediate the nose section and the rear arcuate portion 37, the upper edges of arcuate portions 21, 37 being integrally joined to the lower edge of the main body.

Figure 5:
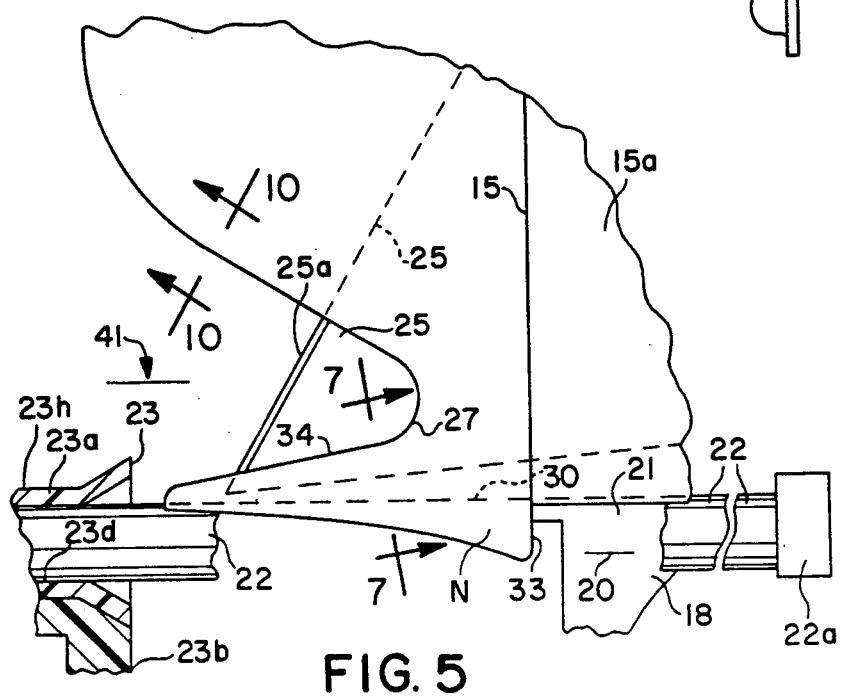
FIG. 5 is an enlarged view of part of the slitter shown in FIG. 3.
Figure 10:
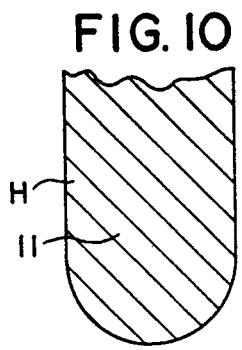
FIG. 10 is a fragmentary cross sectional view that is generally taken along the line and in the direction of the arrows 10—10 of FIGS. 5 and 6.

The location of the axially extending end of the strap section that is integrally joined to the main body is in part indicated by line 20 in FIG. 5 and extends axially rearwardly from the nose portion. When only the main body is being held, the strap section initially extends slightly transversely outwardly and downwardly and then generally downwardly of the handle section and the arcuate section portion such as shown in FIG. 2. The axial dimension (width) of the strap section is substantially less than the length dimension which extends generally perpendicular to the axial dimension (strap section downwardly from the arcuate portion 21 when only the main body is being held). The strap section also includes an intermediate length part 18a that extends intermediate the main clamp portion (handle element) 16 and the arcuate section portion 21. At least the intermediate part is of a flexibility to be wrap around at least the major part of the outer peripheral wall of the catheter, generally designated 22.

The handle element 16 is sufficiently rigid that it retains its shape during normal use. However, as may be seen in FIG. 2, the strap section 18 is of a thickness that is many times less than the corresponding thickness of the main body transversely between the handle member surface 11b and the cutout surface 15a and of a smaller thickness than that of the part 16, for example by a factor of, for example about ¼ to ⅛. Further the above thickness of the main body is, for example, about twice as great as that of the clamp portion 16. The above thickness dimensions are exclusive of the thickness dimensions of the ribs. As a result, the intermediate strap part 18a may be readily at least substantially wrapped around the catheter 22. That is the part 18a is of a flexibility that, for example if the handle section were rotated 90° clockwise from the vertical position of FIG. 2, part 18 initially would extend arcuately upwardly and transversely outwardly and thence extend downwardly under its own weight. The strap section forms a combined hinge and arcuately curved portion for cooperating with the arcuate section N, 21, 37 for clampingly holding the catheter in a fixed axial position relative to the main body. With the strap section in depending relationship to the handle section such as shown in FIGS. 1–3, the axially elongated ribs 19, 20a on members 18, 16 respectively are on the same side of the strap section and main body 11 as the ribs 17. The ribs 12, 13, 17, 19 and 20 are parallel to one another and function as reinforcing members. The surfaces 16a, 18b of the clamp portion 16, strap section 18a which are on the opposite sides of the clamp member T from the ribs 20a, 19 are substantially smooth (no protrusions) as is the corresponding surface 15a of the cutout 15. The length Y of the clamp portion 16 advantageously is about the same as the corresponding dimension X of the cutout.

The handle section has at least the top and rear edge portions of a knife blade 25 embedded therein and at least the lower front corner portion embedded in the nose section. The lower front edge portion of the handle section and the front top portion of the nose section are axially arcuately curved to extend downwardly in a rearwardly inclined direction, and thence reversely curved along front edge portion 27 to extend downwardly and forwardly along the nose section to have part of the cutting edge portion 25a of the blade 25 extend forwardly of the axially adjacent parts of the handle and nose sections. Accordingly the non-embedded portion cutting edge is engagable with the introducer 23 to be slit, and of a dimension in a direction perpendicular to the axial direction (radial dimension), greater than the radial dimension of the thickness of the introducer tubular portion of introducer.

Figure 6:
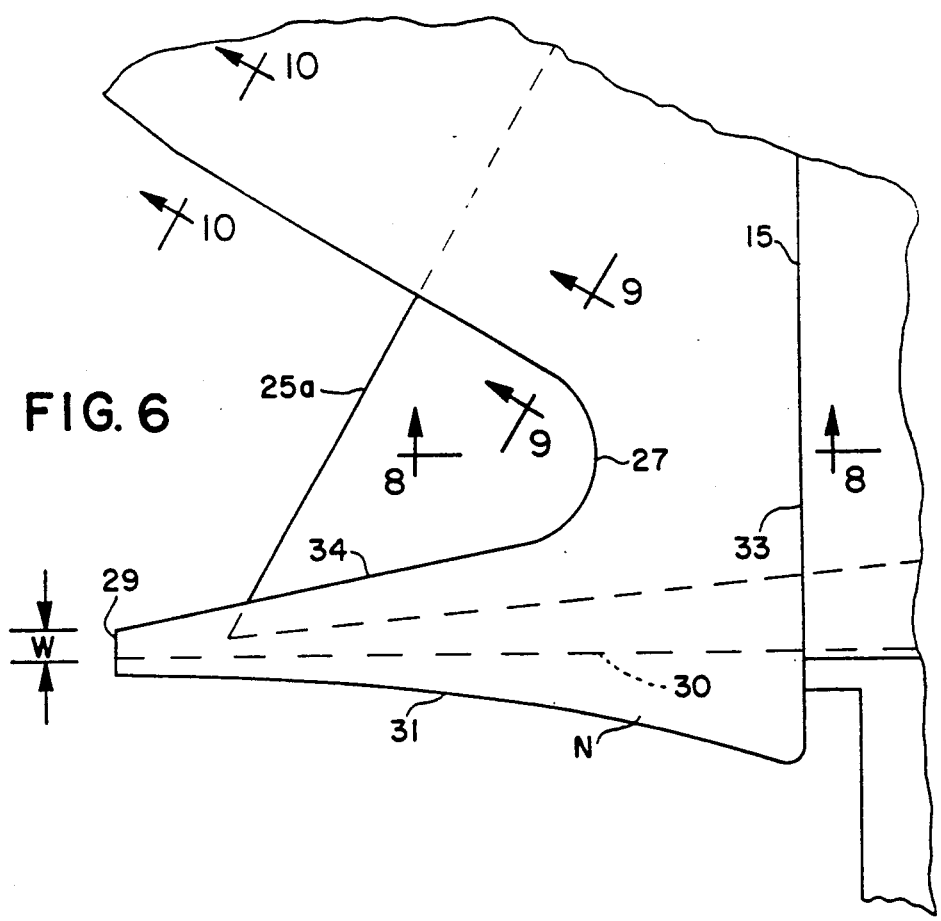
FIG. 6 is a still further enlarged showing of part of structure shown in FIG. 5.

The nose section N in a bottom view is of a generally isometric trapezoidal shape and has a minor base front apex edge 29, a downwardly opening arcuately curved (may be circular curved), axially extending, bottom surface 30 that advantageously is of a slightly larger radius of curvature than the largest outer radius of curvature of catheter the slitter is to be used with. The nose section has an arcuately curved rear edge 33 axially adjacent to the front edge of the cutout 15. Advantageously the catheter abuttable bottom edge (radial inner surface) 21a of part 21 of the arcuate section is of a radius of curvature that is substantially the same as that of the surface 30. The side edges of the nose are arcuately curved in a downward direction while extending predominantly rearwardly. At the juncture of the nose to the handle section, the nose has reinforcing portions 32 that are integrally joined to the handle section and extend upwardly to about the same elevation as the top exposed part of the cutting edge. As seen in FIG. 6 the top surface 34 at the transverse center part of the nose extends axially rearwardly in an upwardly inclined direction at an angle of, for example 6°–15°. The maximum thickness W and maximum transverse dimension Z from the front apex edge 29 each progressively increase in a rearward direction.

The main body has a generally vertical front edge 28 which may be a short distance forwardly of the front edge of the nose N, the lower part of the front edge forming a juncture with the upper part of the reversely curved edge 27. Edge 27 from the front edge extends downwardly and rearwardly, thence has a reversely curved part and thereafter extends downwardly and forwardly to its juncture with the rear part of the nose.

Just rearwardly of the strap section, the transversely arcuately curved, downwardly opening rear portion 37 of the arcuate section is integrally joined to the main body 11 and is adapted to abut against the catheter. Advantageously the maximum transverse dimension of the bottom surface of portion 37 is about the same as the maximum corresponding dimension of the nose section, and the bottom surfaces of portion 37 and the nose portion are axially aligned and of the same radius of curvature. As shown by FIG. 1, in a rearward direction, the main body bottom edge from the rear edge 37a of the arcuate section part 37 is initially radially outwardly and rearwardly curved and then along 11c extends generally axially rearwardly in substantial radial spaced relationship to the catheter when the bottom surface 21a of the arcuate section portion 21 abuts against the catheter. The maximum transverse dimensions of the nose section and arcuate section part 37 abuttable against a catheter is substantially greater than the corresponding dimension of edge 21a, and according the nose and the arcuate section of part 37 aid in retaining the slitter in a desired position on the catheter while the strap is being wrapped around the catheter.

Figure 11:
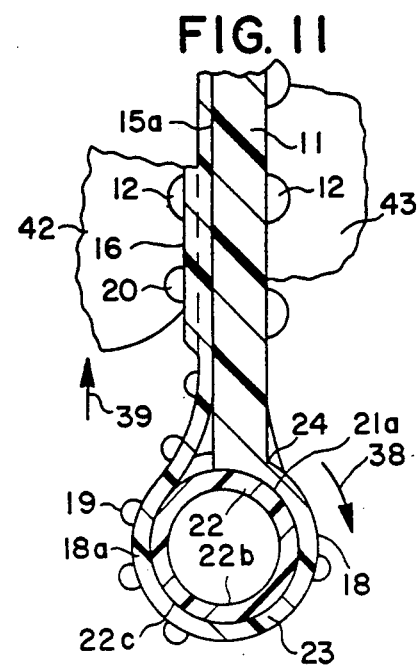
FIG. 11 is a fragmentary cross sectional view generally taken along the line and in the direction of the arrows 11—11 of FIG. 3 other than it shows the strap section in a catheter retaining position to retain a catheter in a fixed axial position relative to the slitter for slitting an introducer on the catheter, said view showing a portion of a rear tubular portion of the introducer prior to being slit.

Since the catheter and introducer advantageously may be the same as those disclosed in U.S. Pat. No. 4,997,424, only fragmentary parts have been shown and said catheter and introducer will not be illustrated and described in detail. As in part shown in FIGS. 5 and 11, the introducer 23 has a tubular portion 23a with inner and outer peripheral walls 23d, 23h and a tab portion 23b at the proximal terminal end of the introducer; while the catheter 22 has inner and outer peripheral walls 22b, 22c and a conventional catheter connector, indicated by the box 22a, at the proximal terminal end of the catheter proximal terminal end. After the catheter or pacing lead 22 has been extended through the introducer 23 into the blood vessel with the axially adjacent parts of the catheter connector and the proximal terminal end of the introducer tube portion axially spaced by a dimension greater than the axial dimension from the edge 37a to the apex edge 29 of first embodiment of the slitter, the slitter is moved radially inwardly to have the surface 21a abut against the catheter with the nose adjacent to the tab portion 23b of the introducer. Now the strap 16, 18 is hingingly swung (wrapped) around the catheter in the direction of the arrow 38 to have its smooth surface 16a in slidably abutting relationship with the cutout surface 15 with the portion 16 and the main body being clamped between the thumb 42 and forefinger 43 of one hand (portions of the thumb and forefinger being shown). At this time, if necessary, the portion 16 can be easily moved radially upwardly (arrow 39) relative to the central axis C—C of the catheter while the slitter is being held by one hand as set forth in the preceding sentence relative to the main body to clampingly grip the catheter to hold the catheter in an axial fixed position relative to the slitter. With the introducer thus being gripped, the introducer tab portion is pulled rearwardly in the direction of the arrow 41 by the other hand such that the rear part of the tubular portion 23a of the introducer is pulled over the nose portion, i.e. the nose portion enters radially between the catheter outer peripheral wall and the tubular portion. Then the proximal terminal edge of the introducer tube portion in being moved rearwardly abuts against the cutting edge to slit the introducer tubular portion and the slitted part of the tubular portion is moved downwardly and rearwardly of the knife edge and the radially adjacent part of the catheter. Since the knife cutting edge portion diverges in a rearward direction and the axially adjacent parts of the main body on opposite sides of the knife diverge in a rearward direction (see FIGS. 8 and 9) the slit edges of the introducer tube portion are transversely spread and thence further spread due to moving downwardly in a rearward direction over the strap section. Thus the introducer is removed from the catheter without having to be pulled over the connector proximal terminal end.

The strap section provides a hinge at its juncture to the arcuate section and thence outwardly therefrom an arcuately curved clamp portion of a length to be bent to in conjunction with the catheter abuttable bottom surface 21a of the arcuate section part 21 extended partially around the catheter and have the clamp portion 16 extend upwardly along the side of the handle section opposite the juncture of the strap section to the arcuate section portion 21 whereby the portion 16 and handle section are firmly held between the user's forefinger and thumb to maintain the catheter in a fixed axial position relative to slitter. The introducer slitter may also be used for slitting an introducer on an electrode head assembly, for example of the type referred in U.S. Pat. No. 4,214,594. However an advantage of the present invention is that it may be used for slitting the tubular portions of introducers of many more different outer diameters than the first embodiment disclosed in U.S. Pat. No. 4,214,594.

Referring to FIGS. 12–14 and 23, the second embodiment of the slitter of this invention, generally designated 45, includes a handle section having an axially elongated main body (handle member) 47 with a generally vertical rear edge 51 and a lower edge integrally joined to the downwardly opening arcuate section 50. An axially elongated clamp member 52, which advantageously may be of about the same axial length as the arcuate section, is integrally joined to one axial and transverse end portion of a transverse tab 55. Further a transverse tab 54 has one axial and transverse end portion integrally joined to at least the rear end of the arcuate section 50 and may be of a height to be joined to the rear edge of the main body 47. The adjacent parts of the rear transverse edges of the tab end portions axially opposite the main body 47 and arcuate section 50 are hingedly connected to one another by a living hinge 57 having a transverse pivot axis. Preferably the transverse width of the hinge is of a transverse dimension many times greater than the thickness of the hinge, for example at least ten times as greater and advantageously many times greater.

The arcuate section and tab 54 have a transversely arcuately curved downwardly opening surface 50b that extends the axial length thereof for cooperating with the transversely arcuately curved surface 52a of the clamp member and tab 55 to clampingly hold a catheter therebetween. Advantageously the radially inner radii of curvature of the surfaces 50b, 52a are such that each transversely extends through an angle of at least about 90 degrees, and desirably more nearly about 180 degrees than 90 degrees for abutting against diametric opposite surfaces of the catheter. Thus the clamp member comprises an arcuate curved portion and when the clamp member and the handle member 47 are in their clamping position, said members clampingly engage diametric opposite outer surfaces of a catheter.

The hinge is transversely offset from the clamp surfaces 50b, 52a to permit the catheter extend rearwardly thereof while the catheter is clampingly engaged by the clamp surfaces 50b, 52a. Additionally the hinge is of a length (dimension along the surface of the hinge from the hinge juncture to the tab 54 to the hinge juncture to the tab 55) to permit spreading the rear end portions of the tabs to permit the slitter being usable with larger diameter catheters and permit the catheter being moved transversely between the tabs 54, 55. The clamp member in being hingingly moved from its non-clamping to its clamping position is generally pivoted in the direction of the arrow 58 about transverse axes generally perpendicular to the catheter central axis.

The knife blade 25 is in part mounted by the arcuate section 50 and the main body. The front edge of the main body includes an upper front edge portion 48 that at its lower end joins with the upper part of the reversely curved front edge portion 49. That is, from the edge portion 48, edge portion 49 extends downwardly and rearward and thence forwardly and downwardly to its juncture with the top surface 50c of the nose M at the transverse center portion thereof. The nose from its front terminal end along its transverse center portion is inclined upwardly, the knife blade 25 at least in part extending forwardly of at least part of the nose and edge 49 whereby as the introducer is pulled rearwardly along the catheter the knife cutting edge engages the introducer tubular portion to slit the tubular portion. Advantageously the radial outer front portion of the nose and the clamp member have their radial outer surfaces diverging in a rearward direction to their inner surfaces and to each other to facilitate the movement of the introducer over said front portions.

In using the second embodiment, the slitter in its unclamped condition can be moved radially relative to the catheter so that it is positioned between the surfaces 50b, 52b, and then the handle section and clamp member moved to a clamped position. The slitter can be easily retained in a clamped position by one hand with one of the section and clamp member bearing against the palm and the other having a clamping force applied thereto by the thumb.

Referring to FIG. 15-17, the third embodiment, generally designated 74, includes a handle section that includes an axially elongated main body (handle member) 75 having a generally vertical front edge potion 78 and a generally vertical rear edge portion 75 having a generally vertical edge 79. Axially intermediate the front edge portion and the rear edge, the main body has a generally rectangular cut out 77 that may be of a transverse depth that is about one half the thickness of the axially adjacent parts of the main body, and opens through the top and bottom edge of the main body. A hinge 81 hingingly connects the transverse adjacent, upper edge parts of the clamp member 80 and the handle member 75 to one another axially intermediate the edge portions 75, 78 for hinging movement about a longitudinal axis. The hinge advantageously is of a greater transversely extending dimension than the thickness thereof and of an axial length that is slightly less than the axial dimension of the cut out 77. Desirably the axial dimension is at least ten times greater than the thickness dimensions. The handle member 80a of the clamp member 80 advantageously is of a size to substantially fill the cut out. The lower terminal axial edges 85d, 80d of the arcuate section 85 and the arcuate portion 80b respectively in a catheter release position are spaced to permit the catheter being moved radially therebetween.

An axially elongated arcuate section 85 is joined (advantageously integrally formed with) to the lower edge of the main body and advantageously is at least the same axial length as that of the main body and may extend axially forwardly of the front edge portion 48. Further the clamp member has an upper portion (handle element) 80a of about the same height and axial dimension as that of the cut out 77 and a lower arcuately curved clamp arcuately curved portion 80b integrally joined to the lower edge of the upper portion 80a and of the same axial dimension as the upper portion. The clamp upper portion has a generally planar surface 80c that abuts against the generally planar surface 77c when the clamp member is in its clamping position with no catheter between the section 85, portion 80b, the surface 77c part defining part of the cut out 77. The handle element and handle member may be readily retained between the thumb and forefinger of one hand of the user to retain the arcuate section and arcuate portion 80b in a catheter clamped position, i.e. the slitter in a fixed position relative to the catheter.

The arcuate section 85 has an axially elongated, arcuately curved radial inner surface 87 that extends the axial length thereof and opens transversely toward the axially elongated, arcuately curved radial inner surface 88 of the curved portion 80b when the clamp member is in its catheter clamping position. When the surfaces 77c, 80c are in abutting relationship, the maximum transverse spacing of surfaces 87, 88 in a horizontal plane perpendicular to surface 77c is less than the outer diameter of the catheter that is to be clampingly held by the slitter. Further the surfaces 87, 88 each extends angularly through at least 90 degrees and are abuttable against diametrically opposite outer surfaces of a catheter being held.

The front end portion of at least the arcuate section defines a nose P having an outer surface (one radially opposite surface 87) that advantageously radially diverges from the surface 87 in an axial rearward direction to facilitate the entry of the nose P between the introducer and the catheter while the outer surface of the front portion of the portion 80b likewise diverges away from surface 88 to facilitate the movement of the then slit introducer rearwardly along the arcuate section and portion 80b. From the nose P, the slitter handle member 74 may be reversely curved along the front edge surface 49 corresponding in side view to that of the second embodiment such that the knife blade 25 which is mounted by the main body and the arcuate section is at least in part located axially forwardly of edge portion 49.

Figure 18:
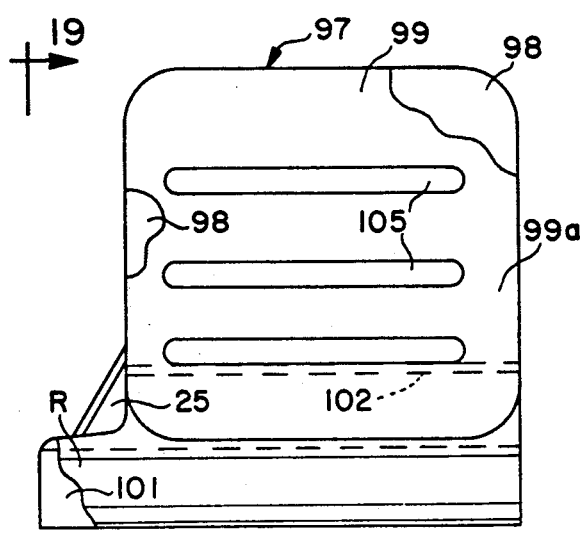
FIG. 18 is a side view of the fourth embodiment of the slitter of this invention.

Referring to FIGS. 18 and 19, the fourth embodiment, generally designated 97, includes a handle section having a generally rectangular, axially elongated main body (handle member) 98 with its lower edge integrally joined to the upper portion of the axially elongated arcuate section 101 which may be of a greater axial length than the main body as in part may be seen in FIG. 18. A clamp member 99 that advantageously is of the same shape as the combination of the main body and arcuate section, but oppositely faced, has a generally rectangular upper portion (handle element) 99a that at is lower portion is integrally joined to the clamp member arcuately curved lower portion 99b. Transversely opposite faces of the main body and the clamp member portion 99a may be provided with longitudinal ribs 105. Adjacent to the juncture of the arcuate section to the main body and the juncture of the upper portion 99a to the arcuately curved portion 99b there is provided a living hinge 102 that hingingly connects the clamp portion to the main body and the arcuate section and has generally axially extending (longitudinal) hinge axes. Desirably the axial length of the hinge is at least ten times that of the thickness of the hinge.

The arcuate section has a radial inner, axially elongated, arcuately curved surface 103 that opens in a general direction toward the arcuate portion 99b while the arcuate portion 99b likewise has a radial inner, axially elongated, arcuately curved surface 104 that opens in a general direction toward surface 103 The surfaces 103, 104 each are arcuately curved through at least 90 degrees and are locate to clampingly abut diametric opposite outer radial surfaces of the smallest catheter that the slitter is to be used with. The front end portions of the arcuate section and the arcuate portion 99b forms a nose R that has radial outer surfaces that advantageously diverge in a rear direction to facilitate the movement of a catheter over the nose as the tubular portion of the introducer is moved rearwardly over the nose. The hinge resiliently urges the movement of the arcuate section and the arcuate portion to a catheter clamping position while the main body and clamp member are manually pivotally movable toward another in the direction of the arrows 100 to release a clamped catheter. The spacing of the surfaces 103, 104 is such that the hinge will resiliently retain said surfaces in abutting relationship to the catheter in an axially fixed position relative thereto as the introducer tubular portion is moved rearwardly on the catheter to slit the tubular portion.

The main body and arcuate section mount a knife blade 25 to extend axially forwardly of the axially adjacent parts of the main body such that the blade will slit the catheter with the entire knife blade being radially outwardly of the slitter surface portions that abut against the catheter.

Referring to FIGS. 20, 21, the fifth embodiment of the slitter, generally designated 110, has handle section 111 that includes a main body (handle member) 111a having its lower edge of integrally joined to its axially elongated arcuate section 112 of the handle section, and a clamp member 113 having an upper portion (handle element) 113a that may be of the same shape as that of the handle section. The clamp member also includes an axially elongated, arcuately curved portion 113b integrally joined to the lower edge of the upper portion 113a. The lower axially edges 112d, 113d of the arcuate section and arcuate portion 113b are integrally joined to the arcuately opposite, axial edges of living hinge, designated by the bracket 114, that resiliently retains the section 112, arcuate portion 113b in their catheter non-clamping (catheter release) position of FIG. 21. The axial length of the hinge is at least ten times that of its thickness while the axial length of the hinge may be the same as that of the arcuate section and arcuate portion.

The arcuate section has a radial inner, axially elongated, arcuately curved surface 128 opening toward the clamp portion 13b, while portion 113b has a radial inner, axially elongated, arcuately curved surface 129 opening toward the surface 128. Advantageously the arcuate section 112, portion 113b and surfaces 128, 129 are of substantially the same axial lengths. Desirably the surfaces extend arcuately through angles of at least 90 degrees and with the smallest outer diameter catheter with which the slitter is to be used, surfaces 128, 129 are clampingly abuttable against diametric opposite surface portions of the catheter.

In the release position, the transverse, axially extending, generally radially extending surfaces of the upper edges 117 and 118 of the arcuate section and curved portion 113b respectively are transversely spaced. Upon hinging moving the main body and clamp upper portion away from one another in the direction opposite arrows 120 to facilitate the catheter being radially moved between the surfaces 117, 118 the edges 117, 118 are moved transversely more remote from one another. In hingingly moving the main body and upper clamp portion toward one another in the direction of the arrows 120 to move the surfaces 117, 118 toward one another, the surfaces 128, 129 are moved to clampingly engage the catheter to retain the catheter in a fixed axial position relative to the slitter. The minimum outer diameter catheter that may be clampingly held is limited by the surfaces 117, 118 being in abutting relationship to one another. A knife blade 123 is mounted by the main body and arcuate section so that the exposed part of the knife blade extends axially forward of the front edge 124 of the main body.

Advantageously the front nose portion T of the section 112, portion 113b have radial outer surfaces that radial outwardly diverge in a rearward direction to facilitate the tubular portion the catheter moving thereover.

Referring to FIG. 22, the sixth embodiment, generally designated 140, is the same as the fifth embodiment other than for the configuration of the main body and the upper clamp portion. That is, in the fifth embodiment the generally planar surfaces 111c of the main body and 113c of the upper clamp portion 113a extend upwardly and outwardly from the vertical, but at opposite angles up to the upper terminal edges thereof, the main body and the upper clamp portion being of the same size and shaped but oppositely faced. The main body (handle member) 141 and the upper clamp portion (handle element) 142 of the sixth embodiment likewise are of the same size and shape but oppositely faced; however instead of extending linearly from the arcuate section 112 and the arcuately curved portion 113, the lower parts 141b of the main body and the lower part 141b of the upper clamp portion diverge in an upward direction at a greater angle than the do the upper part 141a of the main body and the upper part 142a of the upper clamp portion. In fact the adjacent surfaces 141d, 142d of the upper parts 141a, 142a respectively may extend parallel to one another or converge in an upward direction, depending upon the minimum transverse spacing of surfaces 117, 118 from one another. Since the radial outer ends of the main body and upper clamp portion (relative to the central axis of a clamped catheter) of the sixth embodiment are arcuately more closely adjacent to one another than those of the fifth embodiment, in many situation, it is easier to hold the sixth embodiment with one hand than the fifth embodiment during use.

Referring to FIG. 24, the seventh embodiment, generally designated 150, may be the same as the first embodiment except for the differences noted hereinafter. The clamp member (strap) E of the seventh embodiment is joined to the axial intermediate portion of the arcuate section 153, the clamp member including a strap section (clamp portion) 151 which at one axial end is joined to the arcuate section. The opposite axial end of the strap section is joined to the handle element 152 which advantageously may be of nearly the same size and shape as the handle element 16 while the axial dimension of the strap section 151 may be of the same as that of strap section 18. Further the thickness of the section 151 may be substantially the same as that of section 18 exclusive of the thickness dimension of the ribs 19. Instead of the entire slitter being formed in a single molding operation, the strap portion may be formed first and then the handle element joined to the clamp member during the formation of the handle element by a molding operation. Likewise the strap section is similarly joined to the arcuate portion during the molding operation for forming the arcuate portion. The strap section may be made of, for example, Dacron fabric or a thin sheet of plastic. Alternately the strap section may be joined to the handle element and arcuate section in a single molding formation during the formation thereof.

Referring to FIG. 25, the eighth embodiment, generally designated 170, may be the same as the first embodiment or the seventh embodiment, except for the differences noted hereinafter. The clamp member 172 of the eighth embodiment instead of having smooth surfaces 16a, 18b from the juncture of the clamp member T with the arcuate section to the axial terminal edge of the strap section 16 which is remote from the arcuate section has axially extending teeth 172a along at least part of the length thereof that abuts against the main body portion in the catheter clamping position. The part of the clamp member 172 that abuts against the clamped catheter may or may not have teeth 172a, but at least part of the clamp member (part of the member 172 that corresponds to clamp portion 16) has teeth. Additionally, the main body 171 of the eighth embodiment is provided with axially extending teeth 171a that define at least part of the axially extending wall of the main body strap recess 173. As shown in FIG. 25, the upper tooth 171a is located below the top edge of the main body, the planar surface 171b, which corresponds to the upper portion of surface 15 of the first embodiment, extends from the upper tooth to the top edge of the main body 171. Advantageously each tooth 171a has its top axial edge horizontally planar as indicated in FIG. 25, or inclined slightly downwardly and to the right from that shown in FIG. 25. Further, the teeth 172a are shaped to substantially form a mating fit (intermesh) with teeth 171a whereby when the strap portion and main body are in catheter clamping condition the teeth resist movement of the clamp portion relative to the main body portion (in the direction of the arrow 175) to a catheter unclamping condition while offering substantially less resistance to further tightening the clamping engagement (movement of the clamp portion relative to the main body in a direction opposite the arrow 175) with the catheter.

Each of the embodiments may be used for clampingly holding any one of many different outer diameter catheters with the clamping force resulting from one of manually exerting a force to move the main body and upper clamp portion into or toward an abutting engagement, the resilient action of the living hinge, or both. Further, in each of the second through sixth embodiments, the arcuate sections and the clamp arcuately curved portion and the arcuate section of the first embodiment is of sufficient rigidity to maintain substantially the same shapes whether in a clamping or a catheter release position. Additionally, the radial inner surfaces of each of the arcuate sections and the arcuately curved clamp portions may be curved about a single radius emanating from a single point, or a plurality of radii emanating from a plurality of points, but are curved to firm hold a catheter in a fixed position.

With reference to each of the embodiments, the cutting edge of the knife blade extends substantially radially relative the central axis of the portion of the catheter that is clampingly engaged by the slitter. Further, the part of the knife that engages the introducer tubular portion to do the slitting extends further forwardly than any other axially adjacent part of the slitter. Additionally each arcuate section of the embodiments disclosed herein has a nose for extending radially between the clamped catheter and introducer tubular portion and forwardly of the portion of the cutting edge that engages the tubular portion. Also, the width of the hinge (in the direction of the hinge axes) is very much greater than the thickness to minimize, if not prevent, twisting movement of the clamp member relative to the main body as the clamp member hingingly moving between catheter clamping and catheter release positions.

The first, third, fourth, fifth, sixth, seventh and eighth embodiments are preferred over the second embodiment in that it is easily to operate them from a catheter release position to a catheter clamping position and retain them in a catheter clamping position with one hand (primarily with the thumb and forefinger) engaging the slitter than with the second embodiment. In each of the embodiments of the invention, the arcuate section and clamp arcuate portion cooperatively retain the slitter in a fixed axial position relative to a catheter that is clamping engaged by the slitter. In all of the embodiments the radial inner edge of the knife blade is radially outwardly of the radial inner surface of the arcuate section that is abuttable against the catheter.

Desirably, other than for the knife, each embodiment of the slitter is made as a single integrally formed piece of plastic and may be molded in a single step with the knife being embedded during the molding step. It is to be understood that the cutting edge may be formed of plastic during the molding step. Additionally the hinge of each of the second through the sixth embodiment is what is known as a "living hinge".

Also, advantageously the axial dimension of each embodiment of the hinge other the second embodiment, and the transverse dimension of the second embodiment is at least two to five times that of the outer diameter of the tubular portion of the catheters with which the slitter is to be used with. That is, with smaller diameter catheters it is desirably that the axial dimension be larger than for larger diameter catheters in order to prevent twisting of the catheter relative the main body during the period of time that the catheter is being clamped and the introducer is being slit.

What is claimed is:

1. An introducer slitter for facilitating the removal of an introducer from a catheter or pacer lead of one of a number of different outer diameters and extends through the introducer without sliding the introducer over the proximal end of the catheter wherein the catheter and introducer each has an axially elongated tubular portion with inner and outer peripheral walls, comprising a handle section that has a front edge portion and includes an axially elongated handle member having an axially extending lower edge and an axially extending arcuate section joined to the handle member lower edge and having a radial inner surface for abutting against the catheter outer peripheral surface, a clamp member having a front edge and clamp means for clampingly abutting against the catheter outer peripheral surface generally diametrically opposite the arcuate section, hinge means connecting the handle section to the clamp member for hinging movement relative to the handle section between a catheter clamping position that the arcuate section and clamp member cooperatively clamping engage the catheter to retain the catheter in a axially fixed clamped position relative to the slitter and a catheter release position, and mean defining a cutting edge joined to one of the clamp member and the handle section to extend forwardly of the axially adjacent part of the respective one of the clamp member and the handle section front edge portion to which the cutting edge defining means is joined and extending radially outwardly of the arcuate section radial inner surface when the handle section and clamp member are in their clamping position, the one of the handle section and clamp member which has the cutting edge defining means joined thereto having a front nose portion extending axially forwardly of the cutting edge for entering between the introducer inner wall and the catheter outer peripheral wall as the introducer is pulled rearwardly relative to the catheter tubular portion whereby the cutting edge slits the introducer is pulled in a proximal direction.

2. The slitter of claim 1 further characterized in that the clamp means comprises an axially elongated arcuate portion having an arcuately curved inner surface for abutting against the catheter when the arcuate section and clamp member are in the catheter clamping position each of the arcuate section and arcuate portion have an axially rear portion and that the hinge means is joined to the rear portions to extend rearwardly thereof and has a transverse hinge axis.

3. The slitter of claim 1 further characterized in that the hinge means, clamp member and handle section are of an integral unitary construction and made of plastic.

4. The slitter of claim 1 further characterized in that the clamp member includes a handle element that is joined to the clamp means for moving the clamp means and being manually movable relative to the handle member and manually retained relative to the handle member in one of the arcuate section and clamp member catheter release position and the catheter clamping positions.

5. The slitter of claim 4, further characterized in that the hinge means is joined to the handle section adjacent to the juncture of the handle member to the arcuate section and joined to the clamp member adjacent to the juncture of the handle element to the clamp means.

6. The slitter of claim 5, further characterized in that the clamp means comprises an arcuate portion having a radial inner surface, each of the arcuate section and arcuate portion radial inner surface extending angularly through at least about 90 degrees.

7. The slitter of claim 1 further characterized in that the handle section is axially elongated, that the hinge means has an axially extending hinge axis and that the clamp means comprises a strap section portion of a flexibility for being at least partially wrapped around the catheter in the arcuate section and clamp member catheter clamping position for exerting a clamping force against the catheter and in the release position extending substantially linearly away from the arcuate section.

8. The slitter of claim 9 further characterized in that the strap section portion has an axially extending first edge integrally joined to the arcuate section and an opposite axially extending second edge, and that the clamp member includes a handle element joined to strap section portion second edge for abutting against handle member when the arcuate section and clamp member are in their catheter clamping position.

9. The slitter of claim 8 further characterized in that handle member has axially extending, opposite front and rear edges respectively and a cut out axially intermediate the front and rear edge portions for having the handle element movably extended thereinto to selectively adjust the clamping pressure exerted by the strap section portion on the catheter when the clamp member is in its clamping position.

10. The slitter of claim 1 further characterized in that the clamp means comprises an arcuate portion that has an axially elongated arcuately curved surface for clampingly abutting against the catheter diametrical opposite the arcuate section, and that the clamp member includes a handle element joined to the arcuate portion for being manually moved relative to the handle member to move the arcuate portion relative to the arcuate section between a catheter release position and a catheter clamping position.

11. The slitter of claim 10 further characterized in that the handle element has a lower axial edge portion joined to the arcuate portion, that each of the handle member and handle element has an axially top edge portion and that the hinge means comprises a hinge strip having one end joined to the handle member top edge portion and an opposite end joined to the handle element top edge portion.

12. The slitter of claim 10 further characterized in that the handle element has a lower axial edge portion joined to the arcuate portion edge portion, that each of the arcuate section and arcuate portion has a lower terminal axial edge, and that the hinge means comprises a hinge strip having one end joined to the handle member adjacent to the juncture of the handle member to the arcuate section and an opposite end joined to the handle element adjacent to the juncture of the handle element to the arcuate portion to permit sufficient separation of the lower edges for the catheter being moved radially therebetween.

13. The slitter of claim 10 further characterized in that the handle element has a lower axial edge portion joined to the above arcuate portion edge portion, that each of the arcuate portion and arcuate section has a terminal, upper, first axial edge and a lower, second axial edge, and that the hinge means comprises a hinge strip having one end joined to the arcuate second axial edge and an opposite end joined to the arcuate portion second axial edge to permit sufficient separation of the upper edges for the catheter being moved radially therebetween.

14. The slitter of claim 10 further characterized in that the arcuate section and the arcuate portion having lower axial terminal edges that are transversely spaced when the arcuate section and clamp member are in the catheter release position.

15. An introducer slitter for facilitating the removal of an introducer from a catheter or pacer lead that extends through the introducer without sliding the introducer over the proximal end of the catheter wherein the catheter and introducer each has an axially elongated tubular portion with inner and outer peripheral walls, comprising a handle section that has a front edge portion and a rear edge portion and includes an axially elongated handle member having an axially extending lower edge and an axially extending arcuate section joined to the handle member lower edge and having a radial inner surface for abutting against the catheter outer peripheral surface, means defining a radial extending cutting edge that is joined to the handle section to extend forwardly of the axially adjacent part of handle section front edge portion and to extend radially outwardly of the arcuate section surface, a clamp member having a strap section of a flexibility for being wrapped partially around the catheter to clampingly abut against the catheter outer peripheral surface generally diametrically opposite the arcuate section, the strap section having a first axial edge and an opposite axial edge, a hinge portion having a first axial edge joined to the arcuate section and an opposite axial edge joined to the strap section first edge and a handle element joined to the strap section opposite edge for being manually moved into abutting relation to the handle member and moving the strap section to clampingly retain the catheter in abutting relationship with the arcuate section surface.

16. The slitter of claim 15 further characterized in that the arcuate section include a front nose portion that in part defines the arcuate section surface and extends forwardly of the cutting edge and a rear arcuate section portion axially opposite the nose portion from the cutting edge and that in part defines the arcuate section surface.

17. The slitter of claim 15 further characterized in that the handle element is of a substantially greater thickness than the thickness of the strap section and that the axial dimension of strap section is more than about two to five times the maximum outer diameter of the catheter to be clamped, that the clamp member has a catheter release position extending generally linearly away from the arcuate section, and that the combined dimension of the joined handle element and strap section in the direction that the clamp member extends away from the arcuate section when extending linearly away from the arcuate section is many times greater than the axial dimension of the strap section.

18. An introducer slitter for facilitating the removal of an introducer from a catheter or pacer lead that extends through the introducer without sliding the introducer over the proximal end of the catheter wherein the catheter and introducer each has an axially elongated tubular portion with inner and outer peripheral walls, comprising a handle section that has a front edge portion and a rear edge portion and includes an axially elongated handle member having an axially extending lower edge and an axially extending arcuate section joined to the handle member lower edge and having a radial inner surface for abutting against the catheter outer peripheral surface, means defining a cutting edge joined to the handle section to front edge portion and being radially outwardly of the arcuate section surface, a clamp member having a strap section of a flexibility for being wrapped partially around the catheter to clampingly abut against the catheter outer peripheral surface generally diametrically opposite the arcuate section, the strap section having a first axial edge and an opposite axial edge, a hinge portion having a first axial edge joined to the arcuate section and an opposite axial edge joined to the strap section first edge and a handle element joined to the strap section opposite edge for being manually moved into abutting relation to the handle member and moving the strap section to clampingly retain the catheter in abutting relationship with the arcuate section surface, the handle member having a top edge and a bottom edge and a generally rectangular cut out axially intermediate the front and rear edge portions that opens through the top and bottom edges for having the handle section extended thereinto for being manually moved by one of the finger and thumb of one hand of the user while the slitter is being held by one hand of the user to change the clamping pressure exerted on the catheter.

* * * * *